United States Patent
Arnold et al.

(10) Patent No.: US 12,404,349 B2
(45) Date of Patent: *Sep. 2, 2025

(54) AMIDE LINKAGES OF SUGAR MOIETIES TO AMINE TERMINATED LEASHES ATTACHED TO CARBOHYDRATE POLYMERS

(71) Applicant: Navidea Biopharmaceuticals, Inc., Columbus, OH (US)

(72) Inventors: Jeffrey Scott Arnold, Andover, MA (US); David A. Ralph, Columbus, OH (US)

(73) Assignee: Navidea Biopharmaceuticals, Inc., Columbus, OH (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/480,242

(22) Filed: Oct. 3, 2023

(65) Prior Publication Data

US 2024/0132630 A1   Apr. 25, 2024

Related U.S. Application Data

(60) Provisional application No. 63/412,804, filed on Oct. 3, 2022.

(51) Int. Cl.
| | | |
|---|---|---|
| *C08B 37/02* | (2006.01) | |
| *A61K 31/717* | (2006.01) | |
| *A61K 31/721* | (2006.01) | |
| *A61K 31/722* | (2006.01) | |
| *A61K 31/728* | (2006.01) | |
| *C08B 37/00* | (2006.01) | |
| *C08B 37/08* | (2006.01) | |

(52) U.S. Cl.
CPC ........ *C08B 37/0021* (2013.01); *A61K 31/717* (2013.01); *A61K 31/721* (2013.01); *A61K 31/722* (2013.01); *A61K 31/728* (2013.01); *C08B 37/003* (2013.01); *C08B 37/0072* (2013.01); *C08B 37/0087* (2013.01)

(58) Field of Classification Search
CPC .. A61K 31/717; A61K 31/721; A61K 31/722; A61K 31/728; C08B 37/0021; C08B 37/003; C08B 37/0072; C08B 37/0087
See application file for complete search history.

(56) References Cited

U.S. PATENT DOCUMENTS

| | | |
|---|---|---|
| 6,409,990 B1 | 6/2002 | Vera |
| 2012/0213700 A1 | 8/2012 | Magneson et al. |
| 2017/0202969 A1* | 7/2017 | Schlesinger ....... A61K 49/0054 |
| 2020/0306381 A1 | 10/2020 | Ralph |
| 2022/0010036 A1 | 1/2022 | Arnold et al. |

FOREIGN PATENT DOCUMENTS

| | | |
|---|---|---|
| WO | 0069473 A2 | 11/2000 |
| WO | 2015013341 A1 | 1/2015 |
| WO | 2016011415 A2 | 1/2016 |
| WO | 2016011419 A1 | 1/2016 |
| WO | 2016118188 A1 | 7/2016 |
| WO | 2023150695 A1 | 8/2023 |

OTHER PUBLICATIONS

Boschi et al., Pharmaceuticals, 2018, 11, 70, 15 pages. (Year: 2018).*
Shriner et al., Chemical Reviews, 1944, 35(3), p. 351-425. (Year: 1944).*
Muller, C.D., "Neo-mannosylated liposomes: Synthesis and interaction with mouse Kupffer cells and resident peritoneal macrophages", Apr. 4, 1989, 9 pages.
Furneaux, Richard H., "New monnotriosides and trimannosides as potential ligands for mannose-specific binding proteins", 2002, 9 pages.
American Chemical Society (ACS), SciFinder CAS 79360-22-8, accessed on Jan. 4, 2024, 6 pages.
American Chemical Society (ACS), SciFinder CAS 79360-19-3, accessed on Jan. 4, 2024, 6 pages.
American Chemical Society (ACS), SciFinder CAS 1151931-74-6, accessed on Jan. 4, 2024, 6 pages.
American Chemical Society (ACS), SciFinder CAS 219840-25-2, accessed on Jan. 4, 2024, 6 pages.
American Chemical Society (ACS), SciFinder CAS 178212-36-7, accessed on Jan. 4, 2024, 6 pages.
American Chemical Society (ACS), SciFinder CAS 125136-32-5, accessed on Jan. 4, 2024, 6 pages.
International Searching Authority, "International Search Report and Written Opinion", Application No. PCT/US23/75835, mailed Feb. 28, 2024, pp. 1-9.

* cited by examiner

*Primary Examiner* — Jonathan S Lau
(74) *Attorney, Agent, or Firm* — Fredrikson & Byron, P.A.

(57) ABSTRACT

Provided are methods of attaching a mannose-binding C-type lectin receptor targeting moiety to a polymeric carbohydrate backbone using an amide linkage. The amide linkage may be found between a leash, such as an amine terminated leash, and the mannose-binding C-type lectin receptor targeting moieties. The compounds and compositions disclosed utilizing the amide linkage provide for highly stable compounds with a significant reduction in loss of mannose-binding C-type lectin receptor targeting moieties from the polymeric carbohydrate backbone.

19 Claims, 2 Drawing Sheets

FIG. 1

PRIOR ART

AMIDE LINKAGES OF SUGAR MOIETIES TO AMINE TERMINATED LEASHES ATTACHED TO CARBOHYDRATE POLYMERS

CROSS REFERENCE TO RELATED APPLICATION(S)

This application claims priority to and the benefit under 35 U.S.C. § 119(e) to U.S. Provisional Application No. 63/412,804, filed Oct. 3, 2022, entitled "Amide Linkages of Sugar Moieties to Amine Terminated Linkers Attached to Carbohydrate Polymers," which is hereby incorporated by reference in its entirety for all purposes.

TECHNICAL FIELD

The disclosure relates to therapeutic and diagnostic constructs, methods of making, and methods of use thereof, and particularly to the attachment of sugar moieties to a polymeric carbohydrate backbone via an amide linkage.

BACKGROUND

Mannosylated amine dextrans (MADs) are being developed as targeted imaging agents and drug delivery vehicles that bind to C-type lectins, especially the mannose receptor (MR or CD206). One example of a MAD, tilmanocept, has been FDA and EMA approved as the active pharmaceutical ingredient in an imaging agent, Lymphoseek®. Lymphoseek® is approved for indications related to identification of sentinel lymph nodes (SLNs) during surgeries to remove cancerous tumors. Tilmanocept is a synthetic molecular construct built on a 10 kDa (Mw) backbone of the carbohydrate, dextran, which is a polymer of glucose. To this dextran backbone, various numbers of amine terminated leashes, typically 30-40, are appended to the hydroxyl groups of the glucose moieties of the 10 kDa dextran. To these amine-terminated linkers, moieties of the chelating agent, DTPA, typically 3-8, are attached. The DTPA moieties permit tilmanocept to be radiolabeled with various radioactive metal ions, such as $^{99m}$technetium (Tc99m), that permit localization of Tc99m-tilmanocept to be detected by handheld gamma probes or by SPECT. After the DTPA is added, the remaining amine terminated linkers are unoccupied and are substrates for the addition of the sugar, mannose. Tilmanocept has between 12-20 mannose moieties attached to a portion of these unoccupied linkers.

In current clinical practice, $^{99m}$technetium labeled tilmanocept (i.e., Lymphoseek®) is injected into a tumor bed or into tissue near a tumor. From there, it enters the tumor's lymphatic drainage and is transported via lymph vessels to the first encountered lymph node, a SLN. Lymph nodes contain large numbers of CD206 expressing macrophages and dendritic cells. Tc$^{99m}$-Tilmanocept binds to the CD206 on these cells and is internalized by receptor mediated endocytosis. The retained radioactivity is detected by the surgical oncologist, who removes the SLN after which the SLN is examined by a pathologist who determines if the SLN contains a nodal metastasis of the tumor.

Figure 1:
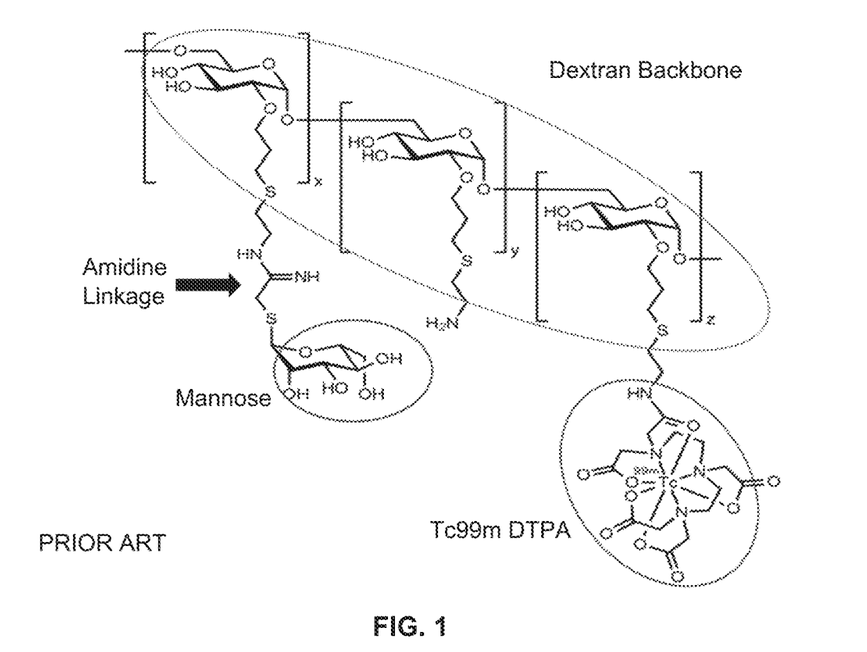
FIG. 1 shows a diagram of the current prior art structure of tilmanocept, including the amidine linkage of mannose to the amine terminated leash on the dextran backbone.

The synthesis of a prototype tilmanocept construct is described in U.S. Pat. No. 6,409,990, hereinafter the "Vera patent", which is hereby incorporated by reference in its entirety. The synthesis protocol described in the Vera patent is still used to make the commercial tilmanocept used in Lymphoseek®. For simplicity, a stylized structure of Tc$^{99m}$-tilmanocept is shown in FIG. 1. However, tilmanocept may differ from the simplified structure shown in FIG. 1 in the following ways: (1) the amine terminated leashes may be attached to any hydroxyl group on the glucose moieties of the dextran backbone; (2) some of the glucose moieties in the dextran backbone do not have any amine terminated leashes attached, and (3) some glucose moieties can have more than one amine terminated leash attached to different hydroxyl groups. While tilmanocept may encompass the above modifications, the current synthesis protocol does not provide for modifications of attaching the mannose moieties to amine terminated leashes.

Under current synthesis protocols, the mannose moieties of tilmanocept are attached to amine terminated leashes via the formation of an amidine linkage. However, the amidine linkage of the mannose moieties has provided a number of challenges. The amidine linkage is unstable in aqueous solutions and especially at alkaline pH. The products of hydrolysis of the amidine linkage include a regeneration of the amine terminated leash and a mannose-related impurity that is undesirable. Further, purifying the mannosylation reaction products by ultrafiltration with water results in the continuous generation of the undesired impurity and continuous reductions in the number of mannose moieties that are retained on the MAD construct. It has been observed in many production batches that the number of retained mannose moieties on the MAD is sufficiently reduced by hydrolysis of the amidine linkages to compromise binding of the MAD to CD206. This result necessitates that the mannosylation reaction be repeated with the MAD. This repeat of the mannosylation reaction is both expensive and time consuming.

Therefore, the current art faces challenges in attaching the same or similar numbers of mannose moieties to a MAD backbone. This lack of control in the chemical synthesis process creates undesirable product variability in the final MAD product (i.e., tilmanocept). The unreliability and irreproducibility of the amidine linkages is highly problematic for the scalability of production for MAD-based therapeutics and diagnostics, which will require many orders of magnitude more product than is currently required for use of tilmanocept as an imaging agent. Furthermore, the instability of the amidine mannose linkage can reduce the shelf-life of tilmanocept and the Lymphoseek® drug product, resulting in waste.

Accordingly, there remains a need for compositions and methods that improve the binding of mannose to a carbohydrate backbone to address the current challenges as identified above.

SUMMARY

Provided herein are compounds and compositions containing a carbohydrate polymeric backbone and mannose moieties attached thereto via an amine terminated leash and amide linker, and methods of making, and methods of using such compounds.

In Example 1, a compound comprises a polymeric carbohydrate backbone comprising at least one amine terminated leash attached thereto, and one or more mannose-binding C-type lectin receptor targeting moieties, wherein the one or more mannose-binding C-type lectin receptor targeting moieties is attached to the amine terminated leash via an amide linker.

Example 2 relates to the compound according to Example 1, wherein the carbohydrate backbone comprises a monosaccharide, disaccharide, or polysaccharide.

Example 3 relates to the compound according to Example 1 or 2, wherein the carbohydrate backbone comprises dextran, cellulose, mannan, chitin, or hyaluronic acid.

Example 3 relates to the compound according to any one of Examples 1 to 3, wherein the compound comprises a subunit as shown in Formula (I):

wherein
each X is independently H, L1-A, L1-Y-A, L2-R, or L3-H, wherein each X is bound to any OH group;
each of L1, L2, and L3 are independently leashes;
each A independently comprises a therapeutic agent, a diagnostic agent, or a theranostic agent;
each Y independently comprises a chelating agent;
each R independently comprises a mannose-binding C-type lectin receptor targeting moiety; and
n is an integer greater than zero, wherein each unit of n may be the same or different;
wherein at least one R is present; and
wherein L2 and R are linked via the amide linker.

Example 5 relates to the compound according to any one of Example 1 to 4, wherein the amine terminated leash comprises a straight or branched chain having about 1 to about 20 member atoms selected from the group consisting of carbon, oxygen, sulfur, nitrogen, and phosphorus.

Example 6 relates to the compound according to any one of Examples 1 to 5, wherein each L2 comprises the following formula:

wherein the bond 1A is attached to a hydroxide group of the polymeric carbohydrate backbone, and wherein y is an integer between 1 and 6.

Example 7 relates to the compound according to any one of Examples 1 to 5, wherein each of L1, L2, or L3 independently comprises —$(CH_2)_pS(CH_2)_q$—NH—, wherein p and q are integers from 0 to 5.

Example 8 relates to the compound according to any one of Examples 1 to 7, wherein L2 does not contain an amidine linkage.

Example 9 relates to the compound according to any one of Examples 1 to 7, wherein the mannose-binding C-type lectin receptor targeting moiety comprises a mannosyl coupling reagent, mannose, high-mannose glycans or mannose oligosaccharides, fucose, n-acetylglucosamine, peptides, galactose, or a combination thereof.

Example 10 relates to the compound according to any one of Examples 1 to 9, wherein at least one subunit of formula (I) comprises:

Example 11 relates to the compound according to any one of Examples 1 to 9, wherein the compound comprises a subunit of formula (Ia):

(Ia)

wherein * indicates the point at which the therapeutic agent, diagnostic agent, or theranostic agent is attached, and wherein y is an integer between 1 and 6.

Example 12 relates to the compound according to any one of Examples 1 to 11, wherein the polymeric carbohydrate backbone has a molecular weight of between about 1 kD to about 150 kD.

In Example 13, a pharmaceutical composition comprises the compound according to any one of Examples 1 to 10, and a pharmaceutically acceptable carrier.

Example 14 relates to the composition according to Example 13, wherein the compound comprises a subunit as shown in Formula (I):

(I)

wherein
each X is independently H, L1-A, L1-Y-A, L2-R, or L3-H, wherein each X is bound to any OH group;
each of L1, L2, and L3 are independently leashes;
each A independently comprises a therapeutic agent, a diagnostic agent, or a theranostic agent;
each Y independently comprises a chelating agent;
each R independently comprises a mannose-binding C-type lectin receptor targeting moiety; and
n is an integer greater than zero, wherein each unit of n may be the same or different;
wherein at least one R is present; and
wherein L2 and R are linked via the amide linker.

Example 15 relates to the composition according to Example 13 or 14, wherein the amine terminated leash comprises a straight or branched chain having about 1 to about 20 member atoms selected from the group consisting of carbon, oxygen, sulfur, nitrogen, and phosphorus.

Example 16 relates to the composition according to any one of Examples 13 to 15, wherein each L2 comprises the following formula:

1A wherein the bond 1A is attached to a hydroxide group of the polymeric carbohydrate backbone, and wherein y is an integer between 1 and 6.

In Example 17, a method of attaching a mannose-binding C-type lectin receptor targeting moiety to a polymeric carbohydrate backbone comprises: (a) synthesizing a mannose-binding C-type lectin receptor targeting moiety comprising an anomeric thio-carboxylate moiety; (b) converting the mannose-binding C-type lectin receptor targeting moiety comprising the anomeric thio-carboxylate moiety into an activated N-hydroxysuccinimide carboxylic acid ester; and (c) reacting the activated N-hydroxysuccinimide carboxylic acid ester with a polymeric carbohydrate backbone having one or more amine terminated leashes attached thereto, wherein the reacting of the activated N-hydroxysuccinimide carboxylic acid ester with the polymeric carbohydrate backbone having one or more amine terminated leashes attached thereto forms an amide linkage between the one or more amine terminated leashes and a carbonyl carbon of the activated N-hydroxysuccinimide carboxylic acid ester.

Example 18 relates to the method according to Example 17, wherein the method retains about 80% of the mannose-binding C-type lectin receptor targeting moieties on the polymeric carbohydrate backbone after about 20 hours.

Example 19 relates to the method according to Example 17 or 18, wherein the dextran backbone has a molecular weight between about 1 kD to about 150 kD.

Example 20 relates to the method according to any one of Examples 17 to 19, wherein the polymeric carbohydrate backbone having one or more amine terminated leashes attached thereto is formed before step (a) or at a point of time between step (a) and (c).

While multiple embodiments are disclosed, still other embodiments of the present disclosure will become apparent to those skilled in the art from the following detailed description, which shows and describes illustrative embodiments of the disclosure. Accordingly, the figures and detailed description are to be regarded as illustrative in nature and not restrictive.

Various embodiments of the present disclosure will be described in detail with reference to the figures. Reference to various embodiments does not limit the scope of the

DETAILED DESCRIPTION OF THE DISCLOSURE

The embodiments of this disclosure are not limited to particular polymeric carbohydrate compositions, which can vary and are understood by skilled artisans. It is further to be understood that all terminology used herein is for the purpose of describing particular embodiments only and is not intended to be limiting in any manner or scope. So that the present disclosure may be more readily understood, certain terms are first defined. Unless defined otherwise, all technical and scientific terms used herein have the same meaning as commonly understood by one of ordinary skill in the art to which embodiments of the disclosure pertain. Many methods and materials similar, modified, or equivalent to those described herein can be used in the practice of the embodiments of the present disclosure without undue experimentation, the preferred materials and methods are described herein. In describing and claiming the embodiments of the present disclosure, the following terminology will be used in accordance with the definitions set out below.

Numeric ranges recited within the specification are inclusive of the numbers defining the range and include each integer within the defined range. Throughout this disclosure, various aspects of this disclosure are presented in a range format. It should be understood that the description in range format is merely for convenience and brevity and should not be construed as an inflexible limitation on the scope of the disclosure. Accordingly, the description of a range should be considered to have specifically disclosed all the possible sub-ranges, fractions, and individual numerical values within that range. For example, description of a range such as from 1 to 6 should be considered to have specifically disclosed sub-ranges such as from 1 to 3, from 1 to 4, from 1 to 5, from 2 to 4, from 2 to 6, from 3 to 6 etc., as well as individual numbers within that range, for example, 1, 2, 3, 4, 5, and 6, and decimals and fractions, for example, 1.2, 3.8, 1½, and 4¾ This applies regardless of the breadth of the range.

The term "about," as used herein, refers to variation in the numerical quantity that can occur, for example, through typical measuring techniques and equipment, with respect to any quantifiable variable, including, but not limited to, mass, volume, temperature, and time. Further, given solid and liquid handling procedures used in the real world, there is certain inadvertent error and variation that is likely through differences in the manufacture, source, or purity of the ingredients used to make the compositions or carry out the methods and the like. Whether or not modified by the term "about," the claims include equivalents to the quantities.

The term "actives" or "percent actives" or "percent by weight actives" or "actives concentration" are used interchangeably herein and refers to the concentration of those ingredients involved in cleaning expressed as a percentage minus inert ingredients such as water or salts. It is also sometimes indicated by a percentage in parentheses, for example, "chemical (10%)."

Disclosed are the components to be used to prepare the compositions of the disclosure as well as the compositions themselves to be used within the methods disclosed herein. These and other materials are disclosed herein, and it is understood that when combinations, subsets, interactions, groups, etc. of these materials are disclosed that while specific reference of each various individual and collective combinations and permutation of these compounds cannot be explicitly disclosed, each is specifically contemplated and described herein. For example, if a particular compound is disclosed and discussed and a number of modifications that can be made to a number of molecules including the compounds are discussed, specifically contemplated is each and every combination and permutation of the compound and the modifications that are possible unless specifically indicated to the contrary.

Thus, if a class of molecules A, B, and C are disclosed as well as a class of molecules D, E, and F and an example of a combination molecule, A-D is disclosed, then even if each is not individually recited each is individually and collectively contemplated meaning combinations, A-E, A-F, B-D, B-E, B-F, C-D, C-E, and C-F are considered disclosed. Likewise, any subset or combination of these is also disclosed. Thus, for example, the sub-group of A-E, B-F, and C-E would be considered disclosed. This concept applies to all aspects of this application including, but not limited to, steps in methods of making and using the compositions of the invention. Thus, if there are a variety of additional steps that can be performed it is understood that each of these additional steps can be performed with any specific embodiment or combination of embodiments of the methods of the invention.

As used herein, the term "pharmaceutically acceptable carrier" or "carrier" refers to sterile aqueous or nonaqueous solutions, colloids, dispersions, suspensions or emulsions, as well as sterile powders for reconstitution into sterile injectable solutions or dispersions just prior to use. Examples of suitable aqueous and nonaqueous carriers, diluents, solvents or vehicles include water, ethanol, polyols (such as glycerol, propylene glycol, polyethylene glycol and the like), carboxymethylcellulose and suitable mixtures thereof, vegetable oils (such as olive oil) and injectable organic esters such as ethyl oleate. Proper fluidity can be maintained, for example, by the use of coating materials such as lecithin, by the maintenance of the required particle size in the case of dispersions and by the use of surfactants. These compositions can also contain adjuvants such as preservatives, wetting agents, emulsifying agents and dispersing agents. Prevention of the action of microorganisms can be ensured by the inclusion of various antibacterial and antifungal agents such as paraben, chlorobutanol, phenol, sorbic acid and the like. It can also be desirable to include isotonic agents such as sugars, sodium chloride and the like. Prolonged absorption of the injectable pharmaceutical form can be brought about by the inclusion of agents, such as aluminum monostearate and gelatin, which delay absorption. Injectable depot forms are made by forming microencapsule matrices of the drug in biodegradable polymers such as polylactide-polyglycolide, poly(orthoesters) and poly(anhydrides). Depending upon the ratio of drug to polymer and the nature of the particular polymer employed, the rate of drug release can be controlled. Depot injectable formulations are also prepared by entrapping the drug in liposomes or microemulsions which are compatible with body tissues. The injectable formulations can be sterilized, for example, by filtration through a bacterial-retaining filter or by incorporating sterilizing agents in the form of sterile solid compositions which can be dissolved or dispersed in sterile water or other sterile injectable media just prior to use. Suitable inert carriers can include sugars such as lactose. Desirably, at least 95% by weight of the particles of the active ingredient have an effective particle size in the range of 0.01 to 10 micrometers.

The term "polarization" is used herein to designate the phenotypic features and the functional features of the macrophages. The phenotype can be defined through the surface markers expressed by the macrophages. The functionality can be defined, for example, based on the nature and the quantity of chemokines and/or cytokines expressed, in particular, secreted by the macrophages. Indeed, the macrophages present different phenotypic and functional features depending of their state, either pro-inflammatory (M1-type) macrophage or anti-inflammatory (M2-type) macrophage. M2-type macrophages can be characterized by the expression of surface markers such as CD206, CD11b, PD-L1 and CD200R and then secretion of cytokines such as CCL17. M1-type macrophages can be defined by the expression of surface markers such as CD86 and CCR7 and the secretion of cytokines such as IL-6, TNF-a and IL12p40. In the context of the present disclosure, the term "repolarize" is used herein to refer to the induction of a change in phenotype of M1 macrophages population to M1-type macrophages.

As used herein, the term "cancer" refers to cells having the capacity for autonomous growth. Examples of such cells include cells having an abnormal state or condition characterized by rapidly proliferating cell growth. The term is meant to include cancerous growths, e.g., tumors; oncogenic processes, metastatic tissues, and malignantly transformed cells, tissues, or organs, irrespective of histopathologic type or stage of invasiveness. Also included are malignancies of the various organ systems, such as respiratory, cardiovascular, renal, reproductive, hematological, neurological, hepatic, gastrointestinal, and endocrine systems; as well as adenocarcinomas which include malignancies such as most colon cancers, renal-cell carcinoma, prostate cancer and/or testicular tumors, non-small cell carcinoma of the lung, cancer of the small intestine, and cancer of the esophagus. Cancer that is "naturally arising" includes any cancer that is not experimentally induced by implantation of cancer cells into a subject, and includes, for example, spontaneously arising cancer, cancer caused by exposure of a patient to a carcinogen(s), cancer resulting from insertion of a transgenic oncogene or knockout of a tumor suppressor gene, and cancer caused by infections, e.g., viral infections. The term "carcinoma" is art recognized and refers to malignancies of epithelial or endocrine tissues. In some embodiments, the present methods can be used to treat a subject having an epithelial cancer, e.g., a solid tumor of epithelial origin, e.g., lung, breast, ovarian, prostate, renal, pancreatic, or colon cancer.

As used herein, the term "subject" refers to the target of administration, e.g., an animal. Thus, the subject of the herein disclosed methods can be a vertebrate, such as a mammal, a fish, a bird, a reptile, or an amphibian. Alternatively, the subject of the herein disclosed methods can be a human, non-human primate, horse, pig, rabbit, dog, sheep, goat, cow, cat, guinea pig or rodent. The term does not denote a particular age or sex. Thus, adult and newborn subjects, as well as fetuses, whether male or female, are intended to be covered. In one aspect, the subject is a mammal. A patient refers to a subject afflicted with a disease or disorder. The term "patient" includes human and veterinary subjects. In some aspects of the disclosed methods, the subject has been diagnosed with a need for treatment of one or more cancer disorders prior to the administering step.

As used herein, the term "synergistic" or "synergistically" means that the effect achieved with the methods and combinations of this invention is greater than the sum of the effects that result from using the compounds, compositions, treatments and/or methods a pharmaceutically acceptable salt thereof, separately. Advantageously, such synergy provides greater efficacy at the same doses, and/or prevents or delays the build-up of multi-drug resistance.

As used herein, the term "treatment" refers to the medical management of a patient with the intent to cure, ameliorate, stabilize, or prevent a disease, pathological condition, or disorder. This term includes active treatment, that is, treatment directed specifically toward the improvement of a disease, pathological condition, or disorder, and also includes causal treatment, that is, treatment directed toward removal of the cause of the associated disease, pathological condition, or disorder. In addition, this term includes palliative treatment, that is, treatment designed for the relief of symptoms rather than the curing of the disease, pathological condition, or disorder; preventative treatment, that is, treatment directed to minimizing or partially or completely inhibiting the development of the associated disease, pathological condition, or disorder; and supportive treatment, that is, treatment employed to supplement another specific therapy directed toward the improvement of the associated disease, pathological condition, or disorder. In various aspects, the term covers any treatment of a subject, including a mammal (e.g., a human), and includes: (i) preventing the disease from occurring in a subject that can be predisposed to the disease but has not yet been diagnosed as having it; (ii) inhibiting the disease, i.e., arresting its development; or (iii) relieving the disease, i.e., causing regression of the disease.

As used herein, the term "diagnosed" means having been subjected to a physical examination by a person of skill, for example, a physician, and found to have a condition that can be diagnosed or treated by the compounds, compositions, or methods disclosed herein. For example, "diagnosed with cancer" means having been subjected to a physical examination by a person of skill, for example, a physician, and found to have a condition that can be diagnosed or treated by a compound or composition that can reduce tumor size or slow rate of tumor growth. A subject having cancer, tumor, or at least one cancer or tumor cell, may be identified using methods known in the art. For example, the anatomical position, gross size, and/or cellular composition of cancer cells or a tumor may be determined using contrast-enhanced MRI or CT. Additional methods for identifying cancer cells can include, but are not limited to, ultrasound, bone scan, surgical biopsy, and biological markers (e.g., serum protein levels and gene expression profiles). An imaging solution comprising a cell-sensitizing composition of the present invention may be used in combination with MRI or CT, for example, to identify cancer cells.

As used herein, the terms "administering" and "administration" refer to any method of providing a pharmaceutical preparation to a subject. Such methods are well known to those skilled in the art and include, but are not limited to, oral administration, transdermal administration, administration by inhalation, nasal administration, topical administration, intravaginal administration, ophthalmic administration, intraaural administration, intracerebral administration, rectal administration, sublingual administration, buccal administration, and parenteral administration, including injectable such as intravenous administration, intra-arterial administration, administration to specific organs through invasion, intramuscular administration, intratumoral administration, and subcutaneous administration. Administration can be continuous or intermittent. In various aspects, a preparation can be administered therapeutically; that is, administered to treat an existing disease or condition. In further various aspects, a preparation can be administered prophylactically; that is, administered for prevention of a disease or condition.

As used herein, the terms "effective amount" and "amount effective" refer to an amount that is sufficient to achieve the desired result or to have an effect on an undesired condition. For example, a "therapeutically effective amount" refers to an amount that is sufficient to achieve the desired therapeutic result or to have an effect on undesired symptoms but is generally insufficient to cause adverse side effects. The specific therapeutically effective dose level for any particular patient will depend upon a variety of factors including the disorder being treated and the severity of the disorder; the specific composition employed; the age, body weight, general health, sex and diet of the patient; the time of administration; the route of administration; the rate of excretion of the specific compound employed; the duration of the treatment; drugs used in combination or coincidental with the specific compound employed and like factors well known in the medical arts. For example, it is well within the skill of the art to start doses of a compound at levels lower than those required to achieve the desired therapeutic effect and to gradually increase the dosage until the desired effect is achieved. If desired, the effective daily dose can be divided into multiple doses for purposes of administration. Consequently, single dose compositions can contain such amounts or submultiples thereof to make up the daily dose. The dosage can be adjusted by the individual physician in the event of any contraindications. Dosage can vary, and can be administered in one or more dose administrations daily, for one or several days. Guidance can be found in the literature for appropriate dosages for given classes of pharmaceutical products. In further various aspects, a preparation can be administered in a "prophylactically effective amount"; that is, an amount effective for prevention of a disease or condition.

Effective dosages may be estimated initially from in vitro assays. For example, an initial dosage for use in animals may be formulated to achieve a circulating blood or serum concentration of active compound that is at or above an IC 50 of the particular compound as measured in an in vitro assay. Calculating dosages to achieve such circulating blood or serum concentrations, taking into account the bioavailability of the particular active agent, is well within the capabilities of skilled artisans. For guidance, the reader is referred to Fingl & Woodbury, "General Principles," In: Goodman and Gilman's The Pharmaceutical Basis of Therapeutics, Chapter 1, pp. 1-46, latest edition, Pergamagon Press, which is hereby incorporated by reference in its entirety, and the references cited therein.

The phrase "anti-cancer composition" can include compositions that exert antineoplastic, chemotherapeutic, antiviral, antimitotic, antitumorgenic, anti-angiogenic, antimetastatic and/or immunotherapeutic effects, e.g., prevent the development, maturation, or spread of neoplastic cells, directly on the tumor cell, e.g., by cytostatic or cytocidal effects, and not indirectly through mechanisms such as biological response modification. There are large numbers of anti-proliferative agents available in commercial use, in clinical evaluation and in pre-clinical development, which could be included in this application by combination drug chemotherapy. For convenience of discussion, anti-proliferative agents are classified into the following classes, subtypes and species: ACE inhibitors, alkylating agents, angiogenesis inhibitors, angiostatin, anthracyclines/DNA intercalators, anti-cancer antibiotics or antibiotic-type agents, antimetabolites, antimetastatic compounds, asparaginases, bisphosphonates, cGMP phosphodiesterase inhibitors, calcium carbonate, cyclooxygenase-2 inhibitors, DHA derivatives, DNA topoisomerase, endostatin, epipodophylotoxins, genistein, hormonal anticancer agents, hydrophilic bile acids (URSO), immunomodulators or immunological agents, integrin antagonists, interferon antagonists or agents, MMP inhibitors, miscellaneous antineoplastic agents, monoclonal antibodies, nitrosoureas, NSAIDs, ornithine decarboxylase inhibitors, pBATTs, radio/chemo sensitizers/protectors, retinoids, selective inhibitors of proliferation and migration of endothelial cells, selenium, stromelysin inhibitors, taxanes, vaccines, and vinca alkaloids. The major categories that some anti-proliferative agents fall into include antimetabolite agents, alkylating agents, antibiotic-type agents, hormonal anticancer agents, immunological agents, interferon-type agents, and a category of miscellaneous antineoplastic agents. Some anti-proliferative agents operate through multiple or unknown mechanisms and can thus be classified into more than one category.

The term "weight percent," "wt. %," "wt-%," "percent by weight," "% by weight," and variations thereof, as used herein, refer to the concentration of a substance as the weight of that substance divided by the total weight of the composition and multiplied by 100.

All publications and patent applications in this specification are indicative of the level of ordinary skill in the art to which this disclosure pertains. All publications and patent applications are herein incorporated by reference to the same extent as if each individual publication or patent application was specifically and individually indicated as incorporated by reference.

Figure 2:
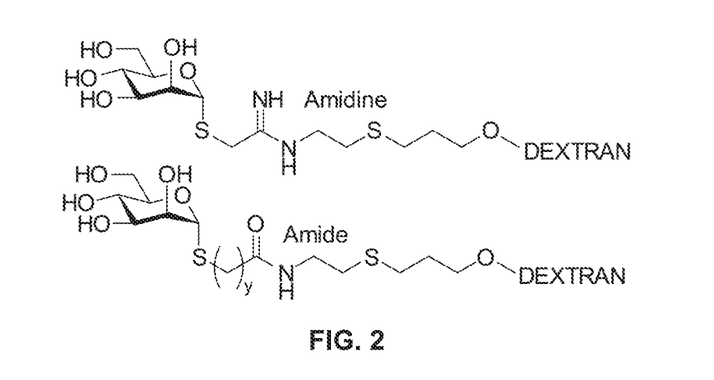
FIG. 2 shows a chemical structure of a MAD construct, showing an amide linkage versus an amidine linkage for attaching a mannose moiety to the amine terminated leashes of MADs.

The present disclosure provides a novel composition of matter for mannosylated polymeric carbohydrate backbones, including MADs such as tilmanocept, and methods to synthesize these new compositions of matter. The present disclosure differs from MAD constructs of the current state of the art, such as those described in the Vera patent, by replacement of the amidine linkage used to attach mannose moieties to the amine terminated leashes of the MADs with an amide linkage. Exemplary examples of the currently used amidine linkage and the amide linkage of the present disclosure are shown in FIG. 2. As described herein, the current use of amidine linkage between the mannose and amine terminated leash results in many stability issues and production challenges. Therefore, in some aspects, it would be preferable to load mannose—or some other mannose-binding C-type lectin receptor targeting moiety—onto a polymeric carbohydrate backbone having a specific and reproducible target range. In beneficial aspects, the amide linked mannose-binding C-type lectin receptor targeting moiety is more stable than the amidine linked mannose-binding C-type lectin receptor targeting moiety, thereby remedying the deficiencies in the current art relative to the instability of the amidine linkages. In embodiments, the use of an amide linker permits greater control in the number of mannose-binding C-type lectin receptor targeting moieties that can be added to the polymeric carbohydrate backbone.

Compounds and Compositions

In certain aspects, compounds disclosed herein employ a carrier construct comprising a polymeric (i.e., carbohydrate) backbone having conjugated thereto mannose-binding C-lectin type receptor targeting moieties (i.e., mannose) to deliver one or more active therapeutic or diagnostic agents. Examples of such polymeric carbohydrate constructs include mannosylated amine dextrans (MADs), which comprise a dextran backbone having mannose molecules conjugated to glucose residues of the backbone and having an active pharmaceutical ingredient conjugated to glucose residues of the backbone. Tilmanocept is a specific example of a MAD. A tilmanocept derivative that is tilmanocept without DTPA conjugated thereto is a further example of a MAD.

MADs are synthetic molecules purposefully designed to be high affinity ligands for mannose-binding C-lectin type receptors, such as, for example, CD206. MADs have been described in U.S. Pat. No. 6,409,990, which is hereby incorporated by reference in its entirety. Thus, the backbone comprises a plurality of glucose moieties (i.e., residues or subunits) primarily linked by α-1,6 glycosidic bonds. Other linkages such as α-1,4 and/or α-1,3 bonds may also be present.

Some embodiments may comprise a backbone that is not a dextran backbone. Some embodiments may have a monosaccharide-based backbone that does not comprise dextran. The backbone of a carbohydrate-based carrier molecules described herein can comprise a glycan other than dextran, wherein the glycan comprises a plurality of monosaccharide residues (i.e., sugar residues or modified sugar residues). In certain embodiments, the glycan backbone has sufficient monosaccharide residues, as well as optional groups such as one or more amino acids, polypeptides and/or lipids, to provide a MW of about 1 to about 50 kDa. As would be appreciated by the skilled artisan when considering the disclosure contained herein, when referring to a "dextran" backbone, other monosaccharide residues may be considered to be substituted in compounds described herein. Additional descriptions of carbohydrate-backbone-based carrier molecules used for targeting CD206 are described in PCT application No. US/2017/055211, which is herein incorporated by reference in its entirety.

In some embodiments, not every backbone moiety is substituted. In some embodiments, one or more leashes are attached to the backbone. In embodiments, mannose-binding C-type lectin receptor targeting moieties are attached to one or more leashes. In certain embodiments, the mannose-binding C-type lectin targeting moieties are attached to between about 15% and about 70%, between about 17% and about 65%, or about 20% and about 60% of the glucose residues via the one or more leashes. In some embodiments, and as further described herein, the one or more leashes may be amine terminated leashes. In further embodiments, the mannose-binding C-type lectin targeting moieties are attached to up to about 60%, up to about 70%, up to about 80%, up to about 90%, or up to about 100% of the glucose residues via the one or more leashes. In certain aspects, the percentages may vary depending on the size of the dextran backbone. In further embodiments, one or more therapeutic, diagnostic, or theranostic agents may optionally be attached to the glucose residues via the one or more leashes. In certain embodiments, the therapeutic agents are attached to between about 1% and about 30%, between about 2% and about 25%, or about 5% and about 20% of the glucose residues via one or more leashes and optional degradable linker, as described herein.

According to certain embodiments, the polymeric carbohydrate constructs disclosed herein contain at least one targeting moiety. In some embodiments, the targeting moiety may be a mannose-binding C-type lectin receptor targeting moiety. In further embodiments, the polymeric carbohydrate constructs disclosed herein contain at least one targeting ligand. CD206 is an example of a C-type lectin receptor expressed on macrophages, dendritic cells, and mesangial cells. CD206 binds to molecules that display multiple terminal mannose moieties. Without being limited to any particular mechanism or theory, it is contemplated that once CD206 binds to a ligand, the receptor/ligand complex is internalized by receptor mediated endocytosis to endosomes that become naturally acidified to a pH of about 4-5. At this lower pH, CD206 releases its ligand and recycles to the cell surface. In some aspects, the inclusion of the mannose-binding C-type lectin receptor targeting moiety within the polymeric carbohydrate construct provides numerous benefits in delivering a therapeutic, diagnostic, or theranostic agent to a target, such as macrophages.

According to some embodiments, the mannose-binding C-type lectin receptor targeting moiety comprises mannose, high-mannose glycans or mannose oligosaccharides, fucose, n-acetylglucosamine, peptides, or galactose. In further embodiments, the mannose-binding C-type lectin receptor targeting moiety comprises mannose. In other embodiments, the at least one targeting ligand may be sialic acid. In embodiments, the mannose-binding C-type lectin receptor targeting moiety is attached to an amine terminated leash via an amide linker. As previously described herein, an exemplary example of the amide linker can be found in FIG. 2. In embodiments, a mannose moiety bearing a carboxylate may be converted into an activated N-hydroxysuccinimide (NHS) carboxylic acid ester followed by a reaction with an amine group of the amine terminated leash to form an amide-linked mannose moiety. In embodiments, once the mannose moiety is linked to the amine terminated leash, the amide linker and amine terminated leash share the same nitrogen as shown in FIG. 2.

As would be understood by those skilled in the art, the number of carbon atoms between the amide moieties of the amide linker and the sulfur atom attached to the C-type lectin receptor targeting moiety (e.g. mannose) can vary as shown in FIG. 2. In some aspects, y is in the range of between about 1 to about 6. In further aspects, y is at least 2. In even further aspects, y is between 1 and 5. Examples of mannosylated polymeric carbohydrate constructs with amide linkages attaching the mannose moieties to the amine terminated leashes have been further synthesized as described in the Examples provided within the disclosure.

As would be understood by those skilled in the art, any sugar, disaccharide, or carbohydrate may be attached to amine terminated leashes on a polymeric carbohydrate backbone using identical chemical methods. Modifying the sugar, disaccharide or carbohydrate attached to the polymeric carbohydrate backbone can create high affinity ligands for a wide variety of receptors besides CD206. As would be understood by those skilled in the art, the chemistry described in the Vera patent for adding amine terminated leashes (or "linkers") to dextran can be used to add amine terminated leashes to any carbohydrate. For example, amine terminated leashes could be added to cellulose, mannan, chitin, or hyaluronic acid by the method of the Vera patent, which is hereby incorporated by reference in its entirety.

In further embodiments, one or more optional therapeutic, diagnostic, or theranostic agents are attached to the glucose residues via a degradable linker. In some embodiments, the degradable linker may comprise an acid sensitive moiety, such as a hydrazone. The use of an acid sensitive linker enables the therapeutic, diagnostic, or theranostic agent to be transported into the cell and allows for the release of the agent substantially inside of the cell. In further embodiments, one or more therapeutic agents are attached to the glucose residues via the amine terminated leashes, as well as a hydrazone linker, which is linked to the backbone using a thiol-maleimide conjugation. In even further embodiments, the therapeutic, diagnostic, or theranostic agents are attached to the glucose residues via a degradable linker comprising one or more carbonate and/or disulfide moieties. In even further embodiments, the therapeutic, diagnostic, or theranostic agent may be attached to the glucose residues via click chemistry, or an azide-alkyne cycloaddition reaction. As provided herein, the degradable linker selected is further conjugated to the amine terminated leashes, which are attached to the polymeric carbohydrate backbone as described herein.

According to certain embodiments, and as further described throughout the disclosure, the one or more mannose-binding C-type lectin receptor targeting moieties and the one or more optional therapeutic, diagnostic, or theranostic agents are each independently attached to the polymeric carbohydrate-based backbone by way of a leash. As described in greater detail below, one or more additional moieties may be present between the leash and the mannose-binding C-type lectin receptor targeting moieties or the therapeutic, diagnostic, or theranostic agent. In some aspects, the one or more additional moieties present between the leash and the mannose-binding C-type lectin receptor targeting moiety or the therapeutic, diagnostic, or theranostic agent comprise linkers, i.e., moieties that link the mannose-binding C-type lectin receptor targeting moiety or the therapeutic, diagnostic, or theranostic agent to the leash.

In further embodiments, the leash is not attached to a mannose-binding C-type lectin receptor targeting moiety or a therapeutic, diagnostic, or theranostic agent, and instead, is provided as a standalone leash attached to the polymeric carbohydrate-based backbone via a connection to one or more hydroxyl groups on the polymeric carbohydrate-based backbone. The leash may be attached to from about 50% to about 100% of the backbone moieties, or from about 70% to about 90% of the backbone moieties. The leashes may be the same or different. In some embodiments, the leash is an amine terminated leash. In some embodiments, the leashes may comprise the formula —(CH$_2$)$_p$S(CH$_2$)$_q$—NH—, wherein p and q are integers from 0 to 5. In further embodiments, the leash comprises the formula —(CH$_2$)$_3$S(CH$_2$)$_2$NH—. In embodiments where the leash is not attached to a mannose-binding C-type lectin receptor targeting moiety or a therapeutic agent, the leash may comprise the formula —(CH$_2$)$_p$S(CH$_2$)$_q$—NH$_2$, wherein p and q are integers from 0 to 5.

In further embodiments, the leash may be a chain of from about 1 to about 20 member atoms selected from carbon, oxygen, sulfur, nitrogen and phosphorus. The leash may be a straight chain or branched. The leash may also be substituted with one or more substituents including, but not limited to, halo groups, perfluoroalkyl groups, perfluoroalkoxy groups, alkyl groups, such C1-4 alkyl, alkenyl groups, such as C$_{1-4}$ alkenyl, alkynyl groups, such as C$_{1-4}$ alkynyl, hydroxy groups, oxo groups, mercapto groups, alkylthio groups, alkoxy groups, nitro groups, azidealkyl groups, aryl or heteroaryl groups, aryloxy or heteroaryloxy groups, aralkyl or heteroaralkyl groups, aralkoxy or heteroaralkoxy groups, HO—(C═O)— groups, heterocyclic groups, cycloalkyl groups, amino groups, alkyl- and dialkylamino groups, carbamoyl groups, alkylcarbonyl groups, alkylcarbonyloxy groups, alkoxycarbonyl groups, alkylaminocarbonyl groups, dialkylamino carbonyl groups, arylcarbonyl groups, aryloxycarbonyl groups, alkylsulfonyl groups, arylsulfonyl groups, —NH—NH$_2$; ═N—H; ═N-alkyl; —SH; —S-alkyl; NH—C(O)—; —NH—C(═N)— and the like. As would be apparent to one skilled in the art, other suitable leashes are possible. In some aspects, the leash used contains an amine group at one end of the leash for purposes of forming an amide linkage with a mannose-binding C-type lectin receptor targeting moiety.

The size of the MAD construct can be varied by changing the size of the initial carbohydrate backbone upon which the construct is assembled. In some embodiments, the backbone of the polymeric carbohydrate-based moiety is between about 1-150 kDa. In other embodiments, the backbone of the polymeric carbohydrate-based moiety is between about 1-100 kDa. In some aspects, the backbone of the polymeric carbohydrate-based moiety may be at least about 50 kDa, at least about 60 kDa, at least about 70 kDa, at least about 80 kDa, or at least about 90 kDa. In other aspects, the polymeric carbohydrate-based moiety may be less than about 100 kDa, less than about 90 kDa, less than about 80 kDa, less than about 70 kDa, or less than about 60 kDa. Alternatively, in some embodiments, the polymeric carbohydrate backbone has a MW of between about 1 kDa and about 50 kDa, while in other embodiments the polymeric carbohydrate backbone has a MW of between about 5 kDa and about 25 kDa. In still other embodiments, the polymeric carbohydrate backbone has a MW of between about 8 kDa and about 15 kDa, such as about 10 kDa. While in other embodiments the polymeric carbohydrate backbone has a MW of between about 1 kDa and about 5 kDa, such as about 3 kDa. Beneficially, the smaller sizes of the disclosed constructs enable greater tumor penetration and greater localization to tumor associated macrophages (TAMs) than is possible with other larger constructs.

As provided throughout the disclosure, the discovery of using an amide linker to attach a mannose-binding C-type lectin receptor targeting moiety to a leash is significant. In aspects, the use of an amide linker permits greater control in the number of mannose-binding C-type lectin receptor targeting moieties that can be added to the polymeric carbohydrate backbone, increasing stability of the polymeric carbohydrate-based constructs and thereby improving scalability. Therefore, the compounds and methods of the disclosure may be incorporated in any polymeric carbohydrate construct requiring the attachment of a mannose-binding C-type lectin receptor targeting moiety onto the polymeric carbohydrate backbone. While any polymeric carbohydrate-based constructs may be considered, the following optional components may be further attached on the polymeric carbohydrate-based compounds of the disclosure.

In some embodiments, the therapeutic, diagnostic, or theranostic agent may be any compound known to be useful for the treatment or diagnosis of a macrophage-mediated disease. In some aspects, a chelating agent may be attached to or incorporated into the disclosed mannosylated carbohydrate polymeric-based compounds. In embodiments, the chelating agent enables labeling of the mannosylated carbohydrate polymeric diagnostic (or imaging) compounds with radioactive metal ions. In further embodiments, the chelating agent may be used to chelate a therapeutic or theranostic agent. Exemplary chelators include but are not limited to diethylenetriamine pentaacetic acid (DTPA), tetraazacyclododecanetetraacetic acid (DOTA), Triethylenetetramine (TETA), {4-[2-(bis-carboxymethylamino)-ethyl]-7carboxymethyl-[1,4,7]-triazonan-1-yl}-acetic acid (NETA), 1,4,7-triazacyclononane-N,N',N''-triacetic acid (NOTA), mercaptoacetylglycylglycyl-glycine (MAG3), dimercaptosuccinic acid, diphenylethylene diamine, porphyrin, iminodiacetic acid, and ethylenediaminetetraacetic acid (EDTA). In embodiments, the chelating agent may be attached to the polymeric carbohydrate backbone via an amine terminated leash. The chelating agent may be further bound to the amine terminated leash via an amide linker. In some embodiments, the chelating agent attached to the carbohydrate polymeric backbone is not further attached to any therapeutic, diagnostic, or theranostic agents. In further embodiments, the mannosylated polymeric carbohydrate compounds may not include a chelating agent.

According to embodiments, the therapeutic agent is a cytotoxic agent. In further embodiments, the therapeutic agent is a chemotherapeutic or anti-cancer agent. In further embodiments, the therapeutic agent may include, but is not limited to, doxorubicin, paclitaxel, bisphosphonates, a metal ion, and anti-inflammatory agents such as dexamethasone. For example, the therapeutic agent may further comprise anti-infective agents, such as antibiotics (e.g. tetracycline, streptomycin, and isoniazid), anti-virals, anti-fungals, and anti-parasitics; immunological adjuvants; steroids; nucleotides, such as DNA, RNA, RNAi, siRNA, CpG or Poly (I:C); peptides; or proteins. In some aspects, the metal ion may include copper, iron, arsenic, antimony silver, cadmium, gallium or gadolinium. In further aspects, the therapeutic agent may further comprise a radioisotope, including but not limited to, $_{99}$mTC, $_{210/212/213/214}$Bi, $^{131}$Ba, $^{140}$Ba, $^{11/14}$C, $^{51}$Cr, $^{67/68}$Ga, $^{153}$Gd, $^{88/90/91}$Y, $^{123/124/125/131}$I, $^{111/115m}$In, $^{18}$F, $^{13}$N, $^{105}$Rh, $^{153}$Sm, $^{67}$Cu, $^{166}$Ho, $^{177}$Lu, $^{223}$Ra, $^{62}$Rb, $^{186/188}$Re, $^{32/33}$P, $^{46/47}$Sc, $^{72/75}$Se, $^{35}$S, $^{89}$Sr, $^{182}$Ta, $^{123m}$Te, $^{127}$Te, $^{129}$Te, $^{132}$Te, $^{65}$Zn, $^{89/95}$Zr; or other chelateable isotope(s). In embodiments, the concentration of the radioisotope may be present in an amount of at least about 100 mCi (millicurie).

In certain embodiments, the therapeutic agent is an anti-microbial drug selected from the group comprising or consisting of: an antibiotic; an anti-tuberculosis antibiotic (such as isoniazid, streptamycin, or ethambutol); an anti-viral or anti-retroviral drug, for example an inhibitor of reverse transcription (such as zidovudin) or a protease inhibitor (such as indinavir); drugs with effect on leishmaniasis (such as Meglumine antimoniate). In certain embodiments, the therapeutic agent is an anti-microbial active, such as amoxicillin, ampicillin, tetracyclines, aminoglycosides (e.g., streptomycin), macrolides (e.g., erythromycin and its relatives), chloramphenicol, ivermectin, rifamycins and polypeptide antibiotics (e.g., polymyxin, bacitracin) and zwittermicin. In certain embodiments, the therapeutic agent is selected from isoniazid, doxorubicin, streptomycin, and tetracycline.

In other embodiments, the therapeutic agent comprises a non-radioactive species selected from, but not limited to, the group consisting of: Bi, Ba, Mg, Ni, Au, Ag, V, Co, Pt, W, Ti, Al, Si, Os, Sn, Br, Mn, Mo, Li, Sb, F, Cr, Ga, Gd, I, Rh, Cu, Fe, P, Se, S, Zn and Zr.

In still further embodiments, the therapeutic agent is selected from the group consisting of cytostatic agents, alkylating agents, antimetabolites, anti-proliferative agents, tubulin binding agents, hormones and hormone antagonists, anthracycline drugs, vinca drugs, mitomycins, bleomycins, cytotoxic nucleosides, pteridine drugs, diynenes, podophyllotoxins, toxic enzymes, and radiosensitizing drugs. By way of more specific example, the therapeutic agent is selected from the group consisting of mechlorethamine, triethylenephosphoramide, cyclophosphamide, ifosfamide, chlorambucil, busulfan, melphalan, triaziquone, nitrosourea compounds, adriamycin, carminomycin, daunorubicin (daunomycin), doxorubicin, isoniazid, indomethacin, gallium(III), 68gallium(III), aminopterin, methotrexate, methopterin, mithramycin, streptonigrin, dichloromethotrexate, mitomycin C, actinomycin-D, porfiromycin, 5-fluorouracil, floxuridine, ftorafur, 6-mercaptopurine, cytarabine, cytosine arabinoside, podophyllotoxin, etoposide, etoposide phosphate, melphalan, vinblastine, vincristine, leurosidine, vindesine, leurosine, taxol, taxane, cytochalasin B, gramicidin D, ethidium bromide, emetine, tenoposide, colchicin, dihydroxy anthracin dione, mitoxantrone, procaine, tetracaine, lidocaine, propranolol, puromycin, ricin subunit A, abrin, diptheria toxin, botulinum, cyanginosins, saxitoxin, shigatoxin, tetanus, tetrodotoxin, trichothecene, verrucologen, corticosteroids, progestins, estrogens, antiestrogens, androgens, aromatase inhibitors, calicheamicin, esperamicins, and dynemicins.

In embodiments wherein the therapeutic agent is a hormone or hormone antagonist, the therapeutic agent may be selected from the group consisting of prednisone, hydroxyprogesterone, medroprogesterone, diethylstilbestrol, tamoxifen, testosterone, and aminogluthetimide.

In embodiments wherein the therapeutic agent is a prodrug, the therapeutic agent may be selected from the group consisting of phosphate-containing prodrugs, thiophosphate-containing prodrugs, sulfate containing prodrugs, peptide containing prodrugs, (-lactam-containing prodrugs, optionally substituted phenoxyacetamide-containing prodrugs, optionally substituted phenylacetamide-containing prodrugs, 5-fluorocytosinem, and 5-fluorouridine prodrugs that can be converted to the more active cytotoxic free drug.

According to further embodiments, any of a variety of detectable moieties can be attached to the carrier molecule, directly or indirectly, for a variety of purposes. As used herein, the term "detectable moiety," "diagnostic moiety," or "diagnostic agent" (which these terms may be used interchangeably) means an atom, isotope, or chemical structure which is: (1) capable of attachment to the carrier molecule; (2) non-toxic to humans; and (3) provides a directly or indirectly detectable signal, particularly a signal which not only can be measured but whose intensity is related (e.g., proportional) to the amount of the detectable moiety. The signal may be detected by any suitable means, including spectroscopic, electrical, optical, magnetic, auditory, radio signal, or palpation detection means as well as by the measurement processes described herein.

Suitable detectable moieties include, but are not limited to radioisotopes (radionuclides), fluorophores, chemiluminescent agents, bioluminescent agents, magnetic moieties (including paramagnetic moieties), metals (e.g., for use as contrast agents), RFID moieties, enzymatic reactants, colorimetric release agents, dyes, and particulate-forming agents. In some aspects, the radioisotopes may be present in an amount of from about 0.01 mCi to about 40 mCi, about 0.05 mCi to about 35 mCi, or about 0.1 mCi to about 30 mCi. By way of specific example, suitable diagnostic moieties include, but are not limited to:

contrast agents suitable for magnetic resonance imaging (MRI), such as gadolinium (Gd3+), paramagnetic and superparamagnetic materials such as superparamagnetic iron oxide;

contrast agents suitable for computed tomographic (CT) imaging, such as iodinated molecules, ytterbium and dysprosium;

radioisotopes suitable for scintigraphic imaging (or scintigraphy) such as $_{99}$mTC, $_{210/212/213/214}$Bi, $^{131}$Ba, $^{140}$Ba, $^{11/14}$C, $^{51}$Cr, $^{67/68}$Ga, $^{153}$Gd, $^{88/90/91}$Y, $^{123/124/125/131}$I, $^{111/115m}$In, $^{18}$F, $^{13}$N, $^{105}$Rh, $^{153}$Sm, $^{67}$Cu, $^{166}$Ho, $^{177}$Lu, $^{223}$Ra, $^{62}$Rb, $^{186/188}$Re, $^{32/33}$P, $^{46/47}$Sc, $^{72/75}$Se, $^{35}$S, $^{89}$Sr, $^{182}$Ta, $^{123m}$Te, $^{127}$Te, $^{129}$Te, $^{132}$Te, $^{65}$Zn, $^{89/95}$Zr; or other chelateable isotope(s);

gamma-emitting agents suitable for single-photon emission computed tomography (SPECT), such as $^{99m}$Tc, $^{111}$In, and $^{123}$I;

dyes and fluorescent agents suitable for optical imaging; and agents suitable for positron emission tomography (PET) such as $^{18}$F.

A diagnostic moiety can be attached to the carrier molecule in a variety of ways, such as by direct attachment or using a chelator attached to a carrier molecule. In some embodiments, diagnostic moieties can be attached using leashes attached to a carrier backbone. In some embodiments, the chelator can be conjugated to an amino group of one or more leashes and can be used to bind the diagnostic moiety thereto. It should be noted that in some instances, glucose moieties of the carbohydrate polymeric backbone may have no attached leash. Certain embodiments may include a single type of diagnostic moiety or a mixture of different diagnostic moieties. For example, an embodiment of a compound disclosed herein may comprise a contrast agent suitable for MRI and a radioisotope suitable for scintigraphic imaging, and further combinations of the diagnostic moieties described herein. In embodiments, after administration of a diagnostic or imaging compound to an animal or human subject, the radioactive metal ions enable single-photon emission computed tomography (SPECT) or positron emission tomography (PET) imagining of anatomical locations or sites where the labeled imaging agents are present.

According to certain embodiments, the disclosed polymeric carbohydrate-based compounds may comprise the formula provided in Formula (I):

(I)

wherein
each X is independently H, L1-A, L1-Y-A, L2-R, or L3-H, wherein each X is bound to any OH group;
each L1, L2, and L3 are independently leashes;
each A independently comprises a therapeutic agent, a diagnostic agent, or a theranostic agent;
each Y independently comprises a chelating agent;
each R independently comprises a mannose-binding C-type lectin receptor targeting moiety; and n is an integer greater than zero, wherein each unit of n may be the same or may be different; and
wherein at least one R is present; and
wherein L2 and R are linked via an amide linker.

In certain embodiments, each of L1, L2, and L3 comprise a degradable leash. In other embodiments, each of L1, L2, and L3 comprise a degradable leash comprising a straight or branched chain of from about 1 to about 20 member atoms selected from carbon, oxygen, sulfur, nitrogen and phosphorus. In further embodiments, each of L1, L2, and L3 may comprise the formula —(CH$_2$)$_p$S(CH$_2$)$_q$—NH—, wherein p and q are independently integers from 0 to 5.

According to further embodiments, at least one of L1,L2, or L3 is a C2-12 hydrocarbon chain optionally interrupted by up to three heteroatoms selected from the group consisting of 0, S and N.

According to some embodiments, each L2 may comprise the following formula:

1A wherein the bond 1A is attached to a hydroxide group of a polymeric carbohydrate backbone, and wherein y is an integer between 1 to 6.

In some aspects, n is an integer greater than zero. In other aspects, n is an integer greater than 1. In further aspects, n may be an integer between 1 and about 50, between about 5 and about 40, or between about 5 and about 30. As would be understood by those skilled in the art, each unit of n may be the same or may be different. As each X may independently be H, L1-A, L1-Y-A, L2-R, or L3-H, each unit of n may consist of any combination of X selected from H, L1-A, L1-Y-A, L2-R, or L3-H.

By way of example only, the mannosylated carbohydrate polymeric therapeutic and diagnostic compound may comprise a unit n having the following formula shown in formula (Ia):

(Ia)

wherein the * indicates the point at which the therapeutic agent or diagnostic agent is attached. In certain embodiments, the therapeutic agent or diagnostic agent is attached at the end of an amino-terminated leash with or without a linker. In further embodiments, a chelating agent may be attached at the end of the amino-terminated leash with or without a linker. The chelating agent may optionally be further attached to a diagnostic agent, therapeutic agent, or theranostic agent. In embodiments, y is an integer between 1 and 6.

By way of a further example, one or more subunits of formula (I) may comprise:

While the structures shown include two carbon atoms between the sulfur atom and amide linkage, as described herein, the carbon chain may range from between 1 and 6 or more.

In certain aspects, the disclosed compounds are present in the form of a pharmaceutical composition in the presence of a pharmaceutically acceptable carrier. In embodiments, the pharmaceutically acceptable carrier employed may be, for example, a solid, liquid, or gas. Examples of solid carriers include lactose, mannitol, microcrystalline cellulose, terra alba, sucrose, talc, gelatin, agar, pectin, acacia, magnesium stearate, and stearic acid. Examples of liquid carriers are sugar syrup, peanut oil, olive oil, ethanol, propylene glycol, and water. Examples of gaseous carriers include carbon dioxide, nitrogen, and compressed air.

In preparing the compositions into a dosage form, any convenient pharmaceutical media can be employed. For example, water, glycols, oils, alcohols, flavoring agents, preservatives, coloring agents and the like can be used to form oral liquid preparations such as suspensions, elixirs and solutions; while carriers such as starches, sugars, microcrystalline cellulose, diluents, granulating agents, lubricants, binders, disintegrating agents, and the like can be used to form oral solid preparations such as powders, capsules and tablets. Because of their ease of administration, tablets and capsules are the preferred oral dosage units whereby solid pharmaceutical carriers are employed. Optionally, tablets can be coated by standard aqueous or nonaqueous techniques. In further aspects, aerosol carriers such as sugars comprising glucose, fructose, mannitol, sucrose, lactose, and cellulose, propellants, liquid carriers, and gaseous carriers may be utilized to form preparations suitable for inhalation. In certain aspects, the compositions are administered intravenously, intraperitoneally, intramuscularly, orally, subcutaneously, intra-tumorally or transdermally. In preferred embodiments, the compositions are administered intravenously.

In embodiments, the composition may include the mannosylated polymeric carbohydrate compound in any therapeutically effective amount as would be appreciated by those skilled in the art. In further embodiments the composition may include the mannosylated polymeric carbohydrate compound in any prophylactically effective amount as would be appreciated by those skilled in the art.

Methods

In some aspects, provided are methods of attaching a mannose-binding C-type lectin receptor targeting moiety to a polymeric carbohydrate backbone as disclosed herein. Beneficially, the mannose-binding C-type lectin receptor targeting moiety may be attached to a polymeric carbohydrate backbone via an amine terminated leash, wherein an amide linker is used to link the mannose-binding C-type lectin receptor targeting moiety to the amine terminated leash. In certain embodiments, the methods of attaching a mannose-binding C-type lectin receptor targeting moiety to a polymeric carbohydrate backbone may comprise the following steps: (a) synthesizing a polymeric carbohydrate backbone having one or more amine terminated leashes attached thereto; (b) obtaining a mannose-binding C-type lectin receptor targeting moiety and reacting it with a mercaptopropionic acid to derivatize the mannose-binding C-type lectin receptor targeting moiety to comprise an anomeric thio-carboxylate moiety; (c) optionally converting the anomeric thio-carboxylate moiety into an activated N-hydroxysuccinimide (NHS) carboxylic acid ester; (d) coupling the activated N-hydroxysuccinimide (NHS) carboxylic acid ester with the polymeric carbohydrate backbone having one or more amine terminated leashes to form an amide linkage (or "linker") between the carbonyl carbon of the activated N-hydroxysuccinimide (NHS) carboxylic acid ester and an amine group of the amine terminated leash.

In an aspect, the steps (a) through (d) do not need to occur in the exact same order. In further aspects, additional steps may occur between each of steps (a) through (d). In some embodiments, step (a) may occur before step (b), (c), or (d), or may occur after step (b) or (c).

In further embodiments, the methods of attaching a mannose-binding C-type lectin receptor targeting moiety to a polymeric carbohydrate backbone may comprise the following steps: (a) synthesizing a mannose-binding C-type lectin receptor targeting moiety comprising an anomeric thio-carboxylate moiety; (b) converting the mannose-binding C-type lectin receptor targeting moiety comprising the anomeric thio-carboxylate moiety into an activated N-hydroxysuccinimide carboxylic acid ester; and (c) reacting the activated N-hydroxysuccinimide carboxylic acid ester with a polymeric carbohydrate backbone having one or more amine terminated leashes attached thereto, wherein the reacting of the activated N-hydroxysuccinimide carboxylic acid ester with the polymeric carbohydrate backbone having one or more amine terminated leashes attached thereto forms an amide linkage between the one or more amine terminated leashes and a carbonyl carbon of the activated N-hydroxysuccinimide carboxylic acid ester.

In an aspect, the polymeric carbohydrate backbone having one or more amine terminated leashes attached thereto is formed before step (a) or at a point of time between step (a) and (c).

In further embodiments, a therapeutic, diagnostic, or theranostic agent may be conjugated to the polymeric carbohydrate backbone prior to, after, or at the same time as attaching the mannose-binding C-type lectin receptor targeting moiety to the polymeric carbohydrate backbone. Additional discussion regarding the methods of attaching the mannose-binding C-type lectin receptor targeting moiety to the polymeric carbohydrate backbone may be found within the non-limiting Examples provided herein.

In certain embodiments, the methods of the disclosure provide for improved stability of the mannosylated polymeric carbohydrate compounds. In some embodiments, the methods provide for mannosylated polymeric carbohydrate compounds that retain at least at least 80%, at least 90%, at least 95%, or at least 98% of the initial mannose-binding C-type lectin receptor targeting moieties attached to the polymeric carbohydrate backbone. In some aspects, the methods achieve the beforementioned retention of the mannose-binding C-type lectin receptor targeting moieties after about 5 hours, after about 10 hours, after about 15 hours, after about 20 hours, after about 25 hours, after about 30 hours, after about 35 hours, or after about 40 hours. In embodiments, the stability is measured at a temperature of between about 20° C. to about 50° C., between about 30° C. to about 45° C., or between about 37° C. to about 42° C.

In certain implementations, the methods of the disclosure further comprise administering to a subject in need thereof an effective dose of the compounds or compositions as disclosed herein. In further embodiments, the methods comprise administering a compound comprising a polymeric carbohydrate backbone, one or more mannose-binding C-type lectin receptor targeting moieties attached to the polymeric carbohydrate backbone via an amide linker, and a therapeutic, diagnostic, or theranostic agent coupled to the polymeric carbohydrate backbone. In even further embodiments, the compound comprises the subunit as provided in Formula (I) disclosed herein.

In certain aspects, the compound is administered in a therapeutically effective amount. In further aspects, the compound is administered in prophylactically effective amount.

In yet further aspects, the methods further comprise administering the compound or composition intravenously, intraperitoneally, intramuscularly, orally, subcutaneously intraocularly, intra-tumor injection or transdermally or delivered directly to tumor organ by invasive techniques.

In still further aspects, the methods further comprise administering the composition in conjunction with at least one other treatment or therapy. In some aspects, the other treatment or therapy comprises an anti-inflammatory agent. In further aspects, the other treatment or therapy comprises co-administering an anti-cancer agent. In further aspects, the other treatment or therapy is chemotherapy. In certain aspects, the compound is administered alone or in combination with other chemical-based therapeutics or with radiation therapy or thermal therapy or physical therapy or dietary therapy.

According to further embodiments, the at least one other treatment or therapy is an immunotherapy, such as, the administration of an immunomodulatory agent. According to certain implementations, the at least one other treatment or therapy is anti-CTLA4 immunotherapy. In certain implementations, the immunomodulatory agent is an immunostimulator. In some embodiments, the immunomodulatory agent is a glucocorticoid, hydrocortisone (cortisol), cortisone acetate, prednisone, prednisolone, methylprednisolone, dexamethasone, betamethasone, triamcinolone, beclometasone, fludrocortisone acetate, deoxycorticosterone acetate (doca) aldosterone, a non-glucocorticoid steroid, a cytostatic agent, an alkylating agent, nitrogen mustard (cyclophosphamide), nitrosourea, a platinum compound, an antimetabolite, a purine analog, azathioprine, mercaptopurine, mycophenolic acid, a pyrimidine synthesis inhibitor, leflunomide, teriflunomide, a folic acid analog, methotrexate, a cytotoxic antibiotic, dactinomycin, anthracyclines, mitomycin C, bleomycin, mithramycin, an antibody or fusion thereof, anti-thymocyte globulin, anti-lymphocyte globulin, an anti-IL-2 receptor antibody, anti-IL6 antibody, an anti-CD3 antibody, OKT3 (muromonab), otelixizumab, teplizumab, visilizumab, an anti-CD4 antibody, clenoliximab, keliximab, zanolimumab, an anti-CD11a antibody, efalizumab, an anti-CD18 antibody, erlizumab, rovelizumab, an anti-CD20 antibody, afutuzumab, ocrelizumab, ofatumumab, pascolizumab, rituximab, an anti-CD23 antibody, lumiliximab, an anti-CD40 antibody, teneliximab, toralizumab, an anti-CD40L antibody, ruplizumab, an anti-CD62L antibody, aselizumab, an anti-CD80 antibody, galiximab, an anti-CD147 antibody, gavilimomab, a B-Lymphocyte stimulator (BLyS) inhibiting antibody, belimumab, an CTLA4-Ig fusion protein, abatacept, belatacept, ipilimumab, tremelimumab, an anti-eotaxin 1 antibody, bertilimumab, an anti-$\alpha$4-integrin antibody, natalizumab, an anti-IL-6R antibody, tocilizumab, an anti-LFA-1 antibody, odulimomab, an anti-CD25 antibody, basiliximab, daclizumab, inolimomab, an anti-CD5 antibody, zolimomab, an anti-CD2 antibody, siplizumab, nerelimomab, faralimomab, atlizumab, atorolimumab, cedelizumab, dorlimomab aritox, dorlixizumab, fontolizumab, gantenerumab, gomiliximab, lebrilizumab, maslimomab, morolimumab, pexelizumab, reslizumab, rovelizumab, talizumab, telimomab aritox, vapaliximab, vepalimomab, aflibercept, alefacept, rilonacept, an immunophilin modulating agent, rapamycin, a calcincurin inhibitor, tacrolimus, ciclosporin (cyclosporin), pimccrolimus, abetimus, gusperimus, ridaforolimus, everolimus, temsirolimus, zotarolimus, a TNF inhibitor, infliximab, adalimumab, certolizumab pegol, golimumab, etanercept, thalidomide, lenalidomide, pentoxifylline, bupropion, curcumin, catechin, an IL-1 receptor antagonist, anakinra, an anti-IL-5 antibody, mepolizumab, an IgE inhibitor, omalizumab, talizumab, an IL12 inhibitor, an IL23 inhibitor, ustekinumab, an opiod, an IMPDH inhibitor, mycophenolic acid, myriocin, fingolimod, an NF-κB inhibitor, raloxifene, drotrecogin alfa, denosumab, an NF-κB signaling cascade inhibitor, disulfiram, olmesartan, dithiocarbamate, a proteasome inhibitor, bortezomib, MG132, Pro1, NPI-0052, curcumin, genistein, resveratrol, parthenolide, thalidomide, lenalidomide, flavopiridol, non-steroidal anti-inflammatory drugs (NSAIDs), arsenic trioxide, dehydroxymethylepoxyquinomycin (DHMEQ), 13C(indole-3-carbinol)/DIM(di-indolmethane) (I3C/DIM), Bay 11-7082, luteolin, cell permeable peptide SN-50, IκBα-super repressor overexpression, NFκB decoy oligodeoxynucleotide (ODN), or a derivative or analog of any thereof.

In exemplary implementations, the combined administration of the compound and the at least one treatment or therapy is synergistically effective relative to administration of either alone.

According to certain embodiments, administration of the compounds disclosed herein in conjunction with another therapy or treatment is associated with reduced toxicity compared to administration of the other therapy or treatment alone. In further embodiments, the co-administration of the instantly disclosed compounds and other therapy or treatment produce a synergic effect. In yet further embodiments, the co-administration of the instantly disclosed compounds and provides for lower effective dose of the other therapy or treatment.

The methods provided herein may be practiced in an adjuvant setting. In some embodiments, the method is practiced in a neoadjuvant setting, i.e., the method may be carried out before the primary/definitive therapy. In some embodiments, the method is used to treat an individual who has previously been treated. Any of the methods of treatment provided herein may be used to treat an individual who has not previously been treated. In some embodiments, the method is used as a first line therapy. In some embodiments, the method is used as a second line therapy.

In further embodiments, a method of treating a disease is provided. In some embodiments, the method comprises administering to a subject in need thereof an effective amount of a compound as disclosed herein. In some aspects, the disease is selected from the group consisting of cancer, an autoimmune disease, an inflammatory disorder, Non-Alcoholic Steatohepatitis (NASH), acute respiratory distress syndrome (ARDS), sepsis, coronavirus infection, influenza infection, cytokine storms, and other macrophage involved diseases.

According to other aspects, the subject has been diagnosed with melanoma, breast cancer, lung carcinoma, pancreatic carcinoma, renal carcinoma, ovarian, prostate or cervical carcinoma, glioblastoma, or colorectal carcinoma, cerebrospinal tumor, head and neck cancer, thymoma, mesothelioma, esophageal cancer, stomach cancer, liver cancer, pancreatic cancer, bile duct cancer, bladder cancer, testicular cancer, germ cell tumor, ovarian cancer, uterine cervical cancer, endometrial cancer, lymphoma, acute leukemia, chronic leukemia, multiple myeloma, sarcoma, or any combination thereof.

In certain aspects, the methods further comprise administering the composition as a bolus and/or at regular intervals. In certain aspects, the disclosed method further comprises administering the composition intravenously, intraperitoneally, intramuscularly, orally, subcutaneously, intra-tumorally or transdermally.

According to certain further embodiments, the method further comprises diagnosing the subject with cancer. In further aspects, the subject is diagnosed with cancer prior to administration of the composition. According to still further aspects, the method further comprises evaluating the efficacy of the composition. In yet further aspects, evaluating the efficacy of the composition comprises measuring tumor size prior to administering the composition and measuring tumor size after administering the compound. In even further aspects, evaluating the efficacy of the composition occurs at regular intervals. According to certain aspects, the disclosed method further comprises optionally adjusting at least one aspect of method. In yet further aspects, adjusting at least one aspect of method comprises changing the dose of the composition, the frequency of administration of the composition, or the route of administration of the compound.

According to certain alternative embodiments, the subject has been diagnosed with a disease associated with elevated levels of CD206+ macrophages and/or MDSC. Such diseases or conditions include, but are not limited to: acquired immune deficiency syndrome (AIDS), acute disseminated encephalomyelitis (ADEM), Addison's disease, agammaglobulinemia, allergic diseases, alopecia areata, Alzheimer's disease, amyotrophic lateral sclerosis, ankylosing spondylitis, antiphospholipid syndrome, antisynthetase syndrome, arterial plaque disorder, asthma, atherosclerosis, atopic allergy, atopic dermatitis, autoimmune aplastic anemia, autoimmune cardiomyopathy, autoimmune enteropathy, autoimmune hemolytic anemia, autoimmune hepatitis, autoimmune hypothyroidism, autoimmune inner ear disease, autoimmune lymphoproliferative syndrome, autoimmune peripheral neuropathy, autoimmune pancreatitis, autoimmune polyendocrine syndrome, autoimmune progesterone dermatitis, autoimmune thrombocytopenic purpura, autoimmune urticarial, autoimmune uveitis, Balo disease/Balo concentric sclerosis, Behcet's disease, Berger's disease, Bickerstaffs encephalitis, Blau syndrome, bullous pemphigoid, Castleman's disease, celiac disease, Chagas disease, chronic inflammatory demyelinating polyneuropathy, chronic recurrent multifocal osteomyelitis, chronic obstructive pulmonary disease, chronic venous stasis ulcers, Churg-Strauss syndrome, cicatricial pemphigoid, Cogan syndrome, cold agglutinin disease, complement component 2 deficiency, contact dermatitis, cranial arteritis, CREST syndrome, Crohn's disease, Cushing's Syndrome, cutaneous leukocytoclastic angiitis, Dego's disease, Dercum's disease, dermatitis herpetiformis, dermatomyositis, Diabetes mellitus type I, Diabetes mellitus type II diffuse cutaneous systemic sclerosis, Dressler's syndrome, drug-induced lupus, discoid lupus erythematosus, eczema, emphysema, endometriosis, enthesitis-related arthritis, eosinophilic fasciitis, eosinophilic gastroenteritis, eosinophilic pneumonia, epidermolysis bullosa acquisita, erythema nodosum, erythroblastosis fetalis, essential mixed cryoglobulinemia, Evan's syndrome, fibrodysplasia ossificans progressiva, fibrosing alveolitis (or idiopathic pulmonary fibrosis), gastritis, gastrointestinal pemphigoid, Gaucher's disease, glomerulonephritis, Goodpasture's syndrome, Graves' disease, Guillain-Barré syndrome (GBS), Hashimoto's encephalopathy, Hashimoto's thyroiditis, heart disease, Henoch-Schonlein purpura, herpes gestationis (aka gestational pemphigoid), hidradenitis suppurativa, HIV infection, Hughes-Stovin syndrome, hypogammaglobulinemia, infectious diseases (including bacterial infectious diseases), idiopathic inflammatory demyelinating diseases, idiopathic pulmonary fibrosis, idiopathic thrombocytopenic purpura, IgA nephropathy, inclusion body myositis, inflammatory arthritis, inflammatory bowel disease, inflammatory dementia, interstitial cystitis, interstitial pneumonitis, juvenile idiopathic arthritis (aka juvenile rheumatoid arthritis), Kawasaki's disease, Lambert-Eaton myasthenic syndrome, leukocytoclastic vasculitis, lichen planus, lichen sclerosus, linear IgA disease (LAD), lupoid hepatitis (aka autoimmune hepatitis), lupus erythematosus, lymphomatoid granulomatosis, Majeed syndrome, malignancies including cancers (e.g., sarcoma, Kaposi's sarcoma, lymphoma, leukemia, carcinoma and melanoma), Meniere's disease, microscopic polyangiitis, Miller-Fisher syndrome, mixed connective tissue disease, morphea, Mucha-Habermann disease (aka Pityriasis lichenoides et varioliformis acuta), multiple sclerosis, myasthenia gravis, myositis, narcolepsy, neuromyelitis optica (aka Devic's disease), neuromyotonia, ocular cicatricial pemphigoid, opsoclonus myoclonus syndrome, Ord's thyroiditis, palindromic rheumatism, PANDAS (pediatric autoimmune neuropsychiatric disorders associated with streptococcus), paraneoplastic cerebellar degeneration, Parkinsonian disorders, paroxysmal nocturnal hemoglobinuria (PNH), Parry Romberg syndrome, Parsonage-Turner syndrome, pars planitis, pemphigus vulgaris, peripheral artery disease, pernicious anaemia, perivenous encephalomyelitis, POEMS syndrome, polyarteritis nodosa, polymyalgia rheumatic, polymyositis, primary biliary cirrhosis, primary sclerosing cholangitis, progressive inflammatory neuropathy, psoriasis, psoriatic arthritis, pyoderma gangrenosum, pure red cell aplasia, Rasmussen's encephalitis, Raynaud phenomenon, relapsing polychondritis, Reiter's syndrome, restenosis, restless leg syndrome, retroperitoneal fibrosis, rheumatoid arthritis, rheumatic fever, sarcoidosis, schizophrenia, Schmidt syndrome, Schnitzler syndrome, scleritis, scleroderma, sepsis, serum Sickness, Sjögren's syndrome, spondyloarthropathy, Still's disease (adult onset), stiff person syndrome, stroke, subacute bacterial endocarditis (SBE), Susac's syndrome, Sweet's syndrome, Sydenham chorea, sympathetic ophthalmia, systemic lupus erythematosus, Takayasu's arteritis, temporal arteritis (aka "giant cell arteritis"), thrombocytopenia, Tolosa-Hunt syndrome,) transplant (e.g., heart/lung transplants) rejection reactions, transverse myelitis, tuberculosis, ulcerative colitis, undifferentiated connective tissue disease, undifferentiated spondyloarthropathy, urticarial vasculitis, vasculitis, vitiligo, and Wegener's granulomatosis.

All publications and patent applications in this specification are indicative of the level of ordinary skill in the art to which this disclosure pertains. All publications and patent applications are herein incorporated by reference to the same extent as if each individual publication or patent application was specifically and individually indicated as incorporated by reference.

EXAMPLES

Embodiments of the present disclosure are further defined in the following non-limiting Examples. It should be understood that these Examples, while indicating certain embodiments of the disclosure, are given by way of illustration only. From the above discussion and these Examples, one skilled in the art can ascertain the essential characteristics of this disclosure, and without departing from the spirit and scope thereof, can make various changes and modifications of the embodiments of the disclosure to adapt it to various usages and conditions. Thus, various modifications of the embodiments of the disclosure, in addition to those shown and described herein, will be apparent to those skilled in the art from the foregoing description. Such modifications are also intended to fall within the scope of the appended claims.

Example 1

An exemplary method of attaching a mannose moiety to a dextran backbone was conducted. Such method was conducted for demonstrating the methods of attaching a mannose moiety to a dextran backbone without limiting the methods to any particular polymeric carbohydrate compound.

Figure 3:
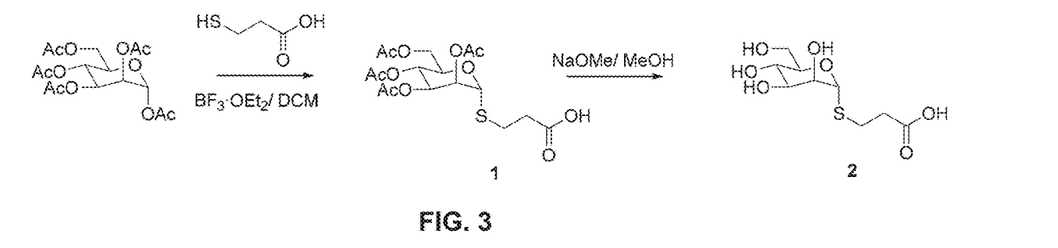
FIG. 3 shows the synthesis of reaction compounds 1 and 2.

3.0 g (7.7 mmol) of pentaacetyl-α-D-mannose and 2.7 ml (31 mmol) of 3-mercaptopropionic acid were combined in 40 ml of anhydrous dichloromethane under nitrogen and cooled on an ice bath. 3.0 ml (29 mmol) of boron trifluoride dietherate was added and solution stirred for 15 hours. The reaction was diluted with dichloromethane, washed with careful addition of water, and followed by washing with saturated sodium bicarbonate. The organics were dried over sodium sulfate, filtered, and concentrated. As shown in FIG. 3, 2.85 g of compound 1 was isolated after silica chromatography using 40% ethyl acetate in hexane and 1% acetic acid. 1.0 g of tetraacetate 1 was solubilized in 16 ml of anhydrous methanol at room temperature and 0.5 ml of 25 wt % sodium methoxide was added. The reaction completion was confirmed by TLC and the pH brought to 3 by addition of acidic resin. The resin was removed by filtration and crude 2 collected by concentration of the filtrate (512 mg). As will be understood by a skilled person in the art, the number of carbons within the anomeric thio-carboxylate moiety in compounds 1 and 2 may be varied.

Figure 4:
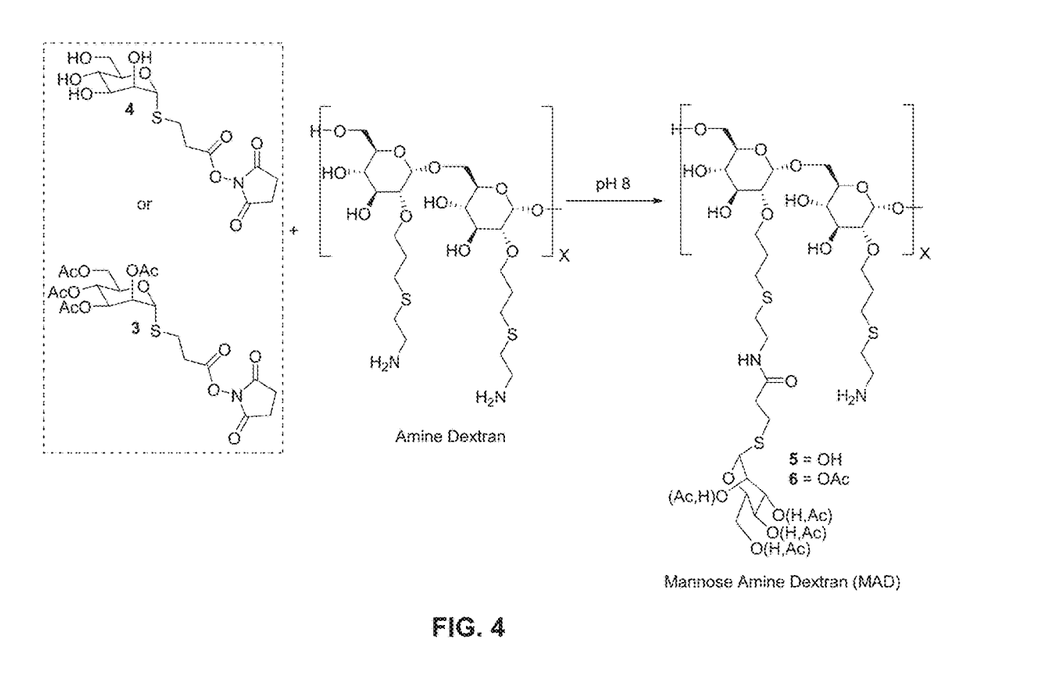
FIG. 4 shows the synthesis of reaction compounds 3, 4, 5 and 6.

Compounds 1 or 2 from FIG. 3 may be converted into activated N-hydroxysuccinimide (NHS) carboxylic acid esters 3 and 4 as shown in FIG. 4 and coupled to amine leashes on dextrans to form the MADs 5 and 6. Coupling of compound 3 required that the acetate protecting groups on mannose were removed while bound to the dextran polymer in a subsequent step.

NHS ester 4 was prepared by dissolving 512 mg (1.9 mmol) of carboxylic acid 2 in 6 ml of anhydrous methanol and adding 14 ml of anhydrous tetrahydrofuran and 14 ml of anhydrous DCM. To this opaque solution was charged 264 ml (2.29 mmol) of NHS and 473 mg (2.29 mmol) of N,N'-dicyclohexylcarbodiimide. The mixture was stirred at room temperature under nitrogen overlay for 15 hours. The reaction was filtered through a glass frit, concentrated, and purified using 20% methanol in DCM on a silica column. 300 mg was isolated as a mixture of activated ester 4 and starting 2.

NHS ester 3 was prepared by dissolving 1.0 g (2.29 mmol) of carboxylic acid 1 and 316 mg (2.75 mmol) of NHS in 15 ml of anhydrous DCM. 527 mg (2.75 mol) of N-(3-Dimethylaminopropyl)-N'-ethylcarbodiimide hydrochloride was added to the solution and stirred for 15 hours. The reaction was diluted with ethyl acetate, washed with water and brine, dried over sodium sulfate, filtered, and concentrated. The process yielded 1.25 g of sufficiently pure NHS ester 3.

Conjugation of Activated ester 4 to Amine Dextran Forming MADs 5: 150 mg of amine dextran (MW 5492) that was prepared from 3.5 kD MW dextran was dissolved at 25 mg/ml in 0.1 M pH 8.3 sodium carbonate buffer. 300 mg of crude NHS ester 4 in 2 ml of methanol was added and stirred overnight. The crude MAD was concentrated and washed with purified water via ultrafiltration using a 3 kDa MWCO membrane and the retentate was frozen and lyophilized. 137 mg of mannose amino dextran as a white foam was isolated with an average of 12.9 bound mannoses per MAD based on 1H NMR integration.

Conjugation of Activated ester 3 to Amine Dextran Forming 6 and Mannose Acetate Removal to 5: 100 mg of amine dextran (MW 5492) that was prepared from 3.5 kD MW dextran was dissolved at 25 mg/ml in 1:1 0.1 M pH 8.3 sodium carbonate buffer and dimethyl sulfoxide (DMSO)

using brief sonication. 194 mg (0.36 mmol) of crude NHS ester 3 in 0.7 ml of DMSO was added to the amino dextran solution in two portions over 4 hours then stirred overnight. The crude and opaque MAD solution was washed with 90% methanol followed by pure methanol via ultrafiltration using a 3 kDa MWCO membrane that resulted in a clear retentate solution of MAD. 6.25 wt-% sodium methoxide in methanol was added dropwise until a basic solution was achieved. The solution became cloudy after ~10 minutes and the mixture was stirred for an additional hour. The mixture was clarified by dilution with purified water and was concentrated via ultrafiltration with four separate volumes of water. After lyophilization, 79 mg of mannose amino dextran 5 as a white foam was isolated with an average of 17 bound mannoses per MAD based on 1H NMR integration.

Example 2

The stability of mannose attached to the polymeric carbohydrate backbone was further evaluated comparing an amide linkage and an amidine linkage between the mannose and the amine terminated leash attached to the dextran backbone of a MAD. The stability of three mannosylated dextrans (MADs) differing by the linkage of mannose to a 10 kDa dextran were compared in solutions of distilled water and 0.1M pH 9.74 aqueous sodium carbonate at 40° C. as shown in Table 1. The MADs were dissolved at 20 mg/ml, sealed in borosilicate glass tubes, and placed in a heating block with agitation. At each respective timepoint, the tube was removed from the heating block and the contents concentrated on a centrifuge using a 3 kDa MWCO spin-filter. The retentate containing the mannosylated dextran was washed three times with distilled water by spin-filtration to remove any hydrolyzed mannose that were no longer bonded to the dextran polymer. The washed retentates were removed from the top of the membrane, frozen, and lyophilized. The mannose number in each sample was determined in $D_2O$ by $^1H$ NMR by setting the integration of the anomeric hydrogens of the dextran polymer between 4.92-5.24 ppm to 1 (average of 61.7 hydrogens in a 10 kDa dextran) and integrating the anomeric hydrogen of the bound mannose at 5.36 ppm.

TABLE 1

| Mannose Linkage in Mannosylated Amine Dextran Compounds | Average Mannose Number per Dextran Chain by $^1H$ NMR | | | |
|---|---|---|---|---|
| | T = 0 hr | T = 20 hr 40° C. in water[1] | T = 44 hr 40° C. in water[1] | T = 20 hr 40° C. in pH 9.74 NaHCO$_3$/ Na$_2$CO$_3$[1] |
| Thiomethyl Amidine (e.g., tilmanocept[2]) | 25.3 | 15.4 | 14.8 | 14.2 |
| Thiomethyl Amide[3] | 23.4 | 22.8 | 23.4 | 23.4 |
| Thioethyl Amide[4], 5 | 21.6 | 23.4 | 21.6 | 22.2 |

[1]MAD Conjugates dissolved at 20 mg/ml.
[2]MAD structure using amidine example in FIG. 2.
[3]Structure shown as amide example in FIG. 2 wherein n = 1.
[4]Stucture shown in FIG. 4, similar to amide example in FIG. 2 wherein n = 2

As shown in Table 1, the MAD compounds using an amide linkage to attach the mannose resulted in surprising stability of the mannose moieties to remain attached to the dextran backbone. The methods used to develop tilmanocept, utilizing an amidine linkage, resulted in a decrease of mannose from 25.3 to 14.2 after 20 hours. Therefore, in order to maintain an adequate number of mannose moieties on the backbone, multiple steps are required to re-attach additional mannose to the polymeric carbohydrate backbone.

On the other hand, both of the MAD compounds utilizing an amide linkage to attach mannose to dextran resulted in nearly no loss of mannose from the dextran backbone. Similar results were observed between the thiomethyl amide and thioethyl amide, demonstrating that the number of carbons between the sulfur atom and amide linkage does not affect the stability of the mannose. The ability of the mannose moieties to remain attached on the dextran backbone results in superior predictability of the produced compounds, increased efficacy of therapeutic and diagnostic use of the compounds for binding to C-type lectin receptors, and increased scalability of production.

The above specification provides a description of the manufacture and use of the disclosed compositions and methods. Since many embodiments can be made without departing from the spirit and scope of the disclosure, the disclosure resides in the claims.

What is claimed is:

1. A compound comprising:
   a polymeric carbohydrate backbone comprising at least one amine terminated leash attached thereto, wherein the at least one amine terminated leash comprises a straight or branched chain having from about 1 to about 20 member atoms selected from the group consisting of carbon, oxygen, sulfur, nitrogen, and phosphorus; and
   one or more mannose-binding C-type lectin receptor targeting moieties,
   wherein the one or more mannose-binding C-type lectin receptor targeting moieties is attached to the at least one amine terminated leash as an amide linkage.

2. The compound of claim 1, wherein the carbohydrate backbone comprises dextran, cellulose, mannan, chitin, or hyaluronic acid.

3. The compound of claim 1, wherein the compound comprises a subunit as shown in Formula (I):

wherein
- each X is independently H, L1-A, L1-Y-A, L2-R, or L3-H, wherein each X is bound to any OH group;
- each of L1, L2, and L3 are independently leashes;
- each A independently comprises a therapeutic agent, a diagnostic agent, or a theranostic agent;
- each Y independently comprises a chelating agent;
- each R independently comprises a mannose-binding C-type lectin receptor targeting moiety attached via a mannosyl coupling moiety; and
- n is an integer greater than zero, wherein each unit of n may be the same or different;
- wherein at least one R is present; and
- wherein at least one L2 is the amine terminated leash to which the mannose-binding C-type lectin receptor targeting moiety is attached via a covalent amide linkage.

4. The compound of claim 3, wherein each L2-R comprises the following formula:

1A wherein the bond 1A is attached to a hydroxide group of the polymeric carbohydrate backbone, wherein A is L2, wherein B is the mannosyl coupling moiety, wherein C is R, and wherein y is an integer between 1 and 6.

5. The compound of claim 4 wherein B and C are attached to A via a precursor molecule of the following formula:

N-Hydroxysuccininide ester   B   C

6. The compound of claim 4 wherein B and C are attached to A via an activated N-hydroxysuccinimide carboxylic acid ester.

7. The compound of claim 3, wherein each of L1, L2, or L3 independently comprises —$(CH_2)_p S(CH_2)_q$—NH—, wherein p and q are integers from 0 to 5.

8. The compound of claim 3, wherein L2 does not contain an amidine linkage.

9. The compound of claim 3, wherein at least one subunit of formula (I) comprises:

or

10. The compound of claim 3, wherein the compound comprises a subunit of formula (Ia):

(Ia)

[Structure Ia shown]

wherein * indicates the point at which the therapeutic agent, diagnostic agent, or theranostic agent is attached, and wherein y is an integer between 1 and 6.

11. The compound of claim 1, wherein the mannose-binding C-type lectin receptor targeting moiety comprises a mannosyl coupling reagent, mannose, high-mannose glycans or mannose oligosaccharides, fucose, N-acetylglucosamine, peptides, galactose, or a combination thereof.

12. The compound of claim 1, wherein the polymeric carbohydrate backbone has a molecular weight of between about 1 kD to about 150 kD.

13. A pharmaceutical composition comprising:
the compound according to claim 1; and
a pharmaceutically acceptable carrier.

14. The composition of claim 13, wherein the compound comprises a subunit as shown in Formula (I):

(I)

[Structure I shown]

wherein
each X is independently H, L1-A, L1-Y-A, L2-R, or L3-H, wherein each X is bound to any OH group;
each of L1, L2, and L3 are independently leashes;
each A independently comprises a therapeutic agent, a diagnostic agent, or a theranostic agent;
each Y independently comprises a chelating agent;
each R independently comprises a mannose-binding C-type lectin receptor targeting moiety attached via a mannosyl coupling moiety; and n is an integer greater than zero, wherein each unit of n may be the same or different;
wherein at least one R is present; and
wherein at least one L2 is the amine terminated leash to which the mannose-binding C-type lectin receptor targeting moiety is attached via a covalent amide linkage.

15. The composition of claim 14, wherein each L2-R comprises the following formula:

1A

[Structure 1A shown]

wherein the bond 1A is attached to a hydroxide group of the polymeric carbohydrate backbone, wherein A is L2, wherein B is the mannosyl coupling moiety, wherein C is R, and wherein y is an integer between 1 and 6.

16. A method of attaching a mannose-binding C-type lectin receptor targeting moiety to a polymeric carbohydrate backbone, comprising:
(a) synthesizing a mannose-binding C-type lectin receptor targeting moiety comprising an anomeric thio-carboxylate moiety;
(b) converting the mannose-binding C-type lectin receptor targeting moiety comprising the anomeric thio-carboxylate moiety into an activated N-hydroxysuccinimide carboxylic acid ester; and
(c) reacting the activated N-hydroxysuccinimide carboxylic acid ester with a polymeric carbohydrate backbone having one or more amine terminated leashes attached thereto, wherein the at least one amine terminated leash comprises a straight or branched chain having from about 1 to about 20 member atoms selected from the group consisting of carbon, oxygen, sulfur, nitrogen, and phosphorus,
wherein the reacting of the activated N-hydroxysuccinimide carboxylic acid ester with the polymeric carbohydrate backbone having one or more amine terminated leashes attached thereto forms an amide linkage between the one or more amine terminated leashes and a carbonyl carbon of the activated N-hydroxysuccinimide carboxylic acid ester.

17. The method of claim 16, wherein the method retains about 80% of the mannose-binding C-type lectin receptor targeting moieties on the polymeric carbohydrate backbone after about 20 hours.

18. The method of claim 16, wherein the dextran backbone has a molecular weight between about 1 kD to about 150 kD.

19. The method of claim 16, wherein the polymeric carbohydrate backbone having one or more amine terminated leashes attached thereto is formed before step (a) or at a point of time between step (a) and (c).

* * * * *